United States Patent [19]
Dickinson, III et al.

[11] 3,938,504
[45] Feb. 17, 1976

[54] METHOD FOR MEASURING VAGINA DIMENSIONS

[76] Inventors: Ben Wade Oakes Dickinson, III, 2125 Broderick St., San Francisco, Calif. 94115; Robert Wayne Dickinson, 40 Maplewood Drive, San Rafael, Calif. 94901

[22] Filed: Oct. 30, 1974

[21] Appl. No.: 519,081

[52] U.S. Cl. .............. 128/2 S; 33/174 D; 128/343; 128/361
[51] Int. Cl.² .......................................... A61B 5/10
[58] Field of Search ............ 128/2 S, 361, 344, 343; 33/174 D, 178 F, 178 R

[56] References Cited
UNITED STATES PATENTS

| | | | |
|---|---|---|---|
| 901,376 | 10/1908 | Roberts | 128/344 X |
| 1,413,789 | 4/1922 | Schaff | 128/344 |
| 2,854,983 | 10/1958 | Baskin | 128/344 X |
| 3,081,765 | 3/1963 | Kompelein | 128/344 X |
| 3,095,871 | 7/1963 | Mann et al. | 128/2 S |
| 3,435,826 | 4/1969 | Fogarty | 128/344 |
| 3,661,148 | 5/1972 | Kolin | 128/2 S X |
| 3,706,307 | 12/1972 | Hasson | 128/2 S |

*Primary Examiner*—Kyle L. Howell
*Attorney, Agent, or Firm*—Flehr, Hohbach, Test, Albritton & Herbert

[57] ABSTRACT

A trial and error method for measuring dimensions of the vagina and specifically the effective diameter of the vaginal sphincter muscle of an animal such as a dog or other female animal, using a plurality of measuring devices having a nose cone portion with a blunt free end mounted to an elongate handle, said nose cone portion including an intermediate ring of maximum diameter. The sphincter muscle diameter is determined by inserting said nose cone portion through the vulva until said intermediate ring passes anterior to the sphincter muscle and thereafter repeating the step of insertion with different measuring devices having increasingly larger diameters until a marked build-up of resistance to anterior movement of the device is detected upon contact of said intermediate ring with the sphincter muscle.

1 Claim, 4 Drawing Figures

U.S. Patent Feb 17, 1976 3,938,504
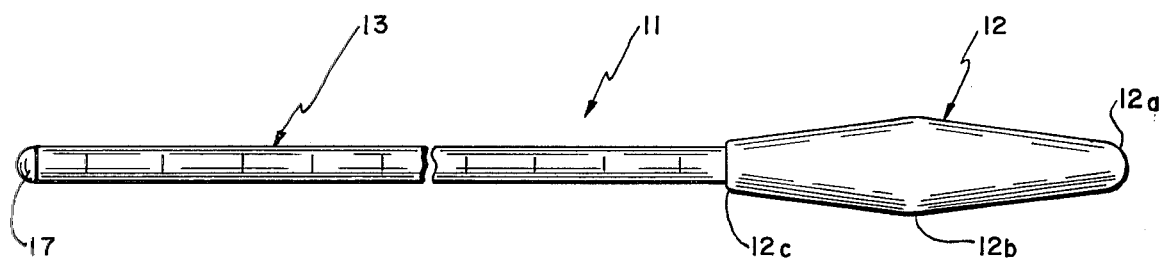
FIG.—1
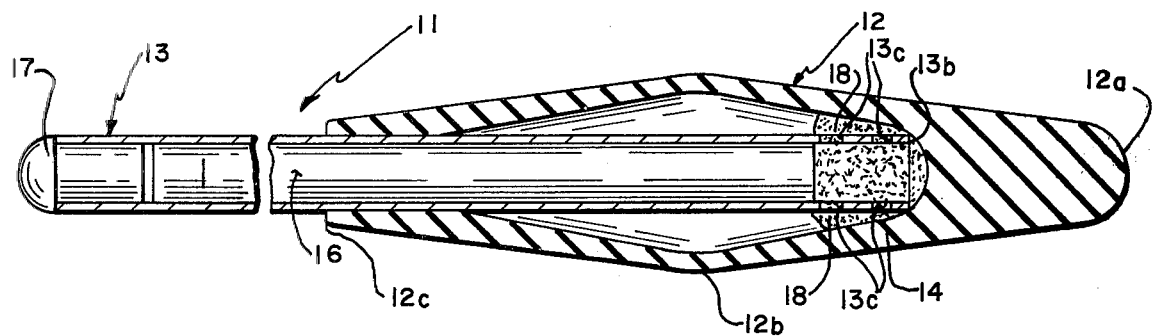
FIG.—2
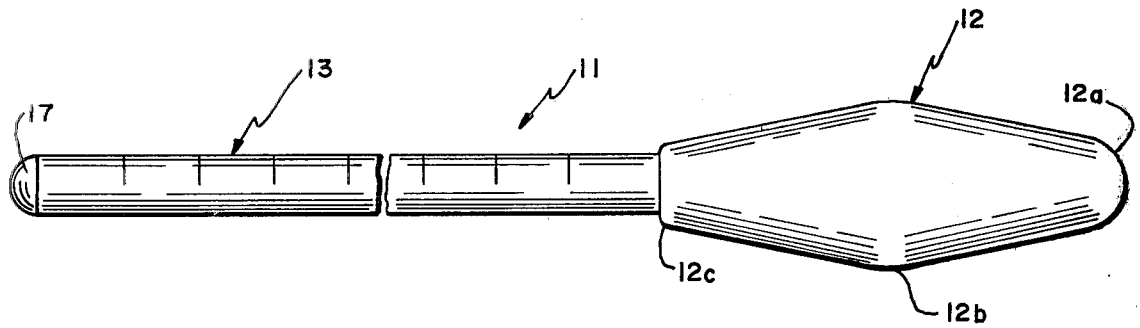
FIG.—3
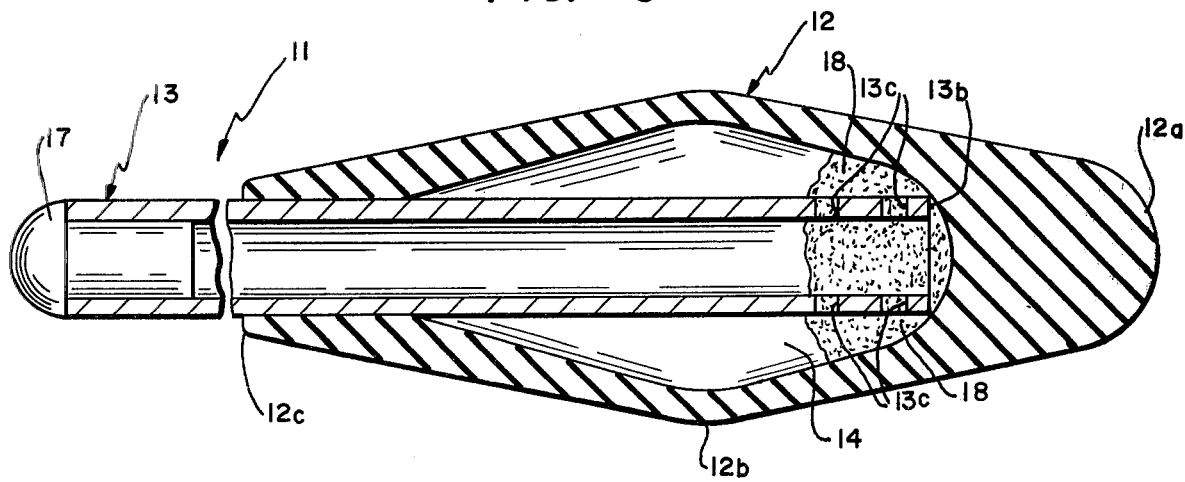
FIG.—4

METHOD FOR MEASURING VAGINA DIMENSIONS

CROSS-REFERENCE TO RELATED APPLICATIONS

Reference is made to our co-pending patent application, U.S. Ser. No. 348,204, filed Apr. 5, 1973, entitled "Intra-Vaginal Device and Method", now U.S. Pat. No. 3,854,476.

BACKGROUND OF THE INVENTION

In an application entitled "Intra-Vaginal Device and Method," Ser. No. 348,204, filed Apr. 5, 1973 now U.S. Pat. No. 3,854,476, incorporated herein by reference, an intra-vaginal contraceptive device is described which includes an elongate member with a disc disposed to the posterior end flexibly coupled to an extension element at the anterior end of the device. The illustrated extension element includes a flexible frusto-conical portion. The length of the overall device and the diameter of the frusto-conical portion vary depending upon the size of the animal's vaginal tract. Because of the size and shape of the disc which assists retention of the device, it would be time consuming and irritating to the animal to make size measurements by trial and error insertions of contraceptive devices of varying sizes. Thus, there is a need for a measuring device which accurately determines the appropriate size of the frusto-conical portion of the contraceptive device in a relatively short period of time without these disadvantages.

SUMMARY OF THE INVENTION AND OBJECTS

It is an object of the invention to provide a method for the measurement of the diameter of the effective vaginal sphincter muscle and the vaginal lumen of an animal which includes such muscle.

It is a further object of the invention to provide a method of measuring the length of the animal's vagina.

It is another object of the invention to provide such a method for measuring the effective size of the contraceptive device described above.

In accordance with the above objects, a measuring device has been provided for insertion into the vagina of a female animal of the type having a vaginal sphincter muscle for purposes of measuring the muscle. The device includes handle means with an elongate stiff, shape-retaining portion and a nose cone concentrically mounted to the elongate portion. The nose cone has a blunted free end tapering in increasing radial extent to an intermediate ring of maximum diameter tapering from the ring in decreasing radial extent to the elongate portion to form opposed concentric frusto-conical portions meeting in a common base. The ring is defined as the section of maximum radial extension through the common base. The handle means is substantially longer than the nose cone to permit the ring to pass anterior of the sphincter muscle while being externally grasped. The nose cone is preferably formed of a flexible material to simulate the flexible frusto-conical portion of the contraceptive device set forth in the above co-pending application.

The above device is grasped by the handle and the nose cone portion is inserted through the animal's vulva into the animal's vagina until the intermediate ring passes anterior to the sphincter muscle. This step is repeated with different measuring instruments having intermediate rings of successively increased diameters. The effective diameter of the sphincter muscle for purposes of the present invention is the one measured by a device which causes a marked build-up of resistance against anterior movement transmitted to the grasped rod upon contact of the ring with the sphincter muscle and a distinct release of the resistance after passage through the muscle.

Additional objects and features of the present invention will be apparent from the following description taken in conjunction with the accompanying drawing.

BRIEF DESCRIPTION OF THE DRAWING

FIGS. 1 and 3 are side elevational views, partially broken away, of different measuring devices according to the invention.

FIGS. 2 and 4 are cross-sectional views, partially broken away, of the devices illustrated in FIGS. 1 and 3, respectively.

DETAILED DESCRIPTION OF THE PREFERRED EMBODIMENTS

The measuring device of the present invention is utilized for measuring the sphincter muscle of a female animal of the type having its vagina terminating at the posterior end in a normally closed vulva and at the anterior end in a normally closed cervix with a vaginal sphincter muscle therebetween. Animals of the foregoing type include dogs, cats, hogs, horses, sheep, cows, and the like. The device is particularly well suited for use in the dog. Although it is to be understood that the invention also relates to measuring devices for animals, especially the cat, appropriate modifications are made to accomodate the difference of the internal anatomy of the cat's reproductive tract.

Referring to the drawing, a measuring device, generally designated by the number 11, is illustrated which includes a nose cone portion 12 and handle means in the form of an elongate rod portion 13. This latter portion is broken away to illustrate its relatively long length in comparison to the length of the nose cone. Rod portion 13 is typically at least two to four times longer than nose cone portion 12.

Nose cone portion 12 includes a blunted free end 12a tapering in increasing radial extent to an intermediate ring 12b of maximum diameter and from there in decreasing radial extent to contact the surface of the elongate portion 13 at edge 12c. Thus, the nose cone portion includes continuous opposed concentric frusto-conical portions meeting in a common base at ring 12b. To minimize irritation during use, substantial interruption in the continuity of the surface of the nose cone and the inserted segment of rod portion 13 is to be avoided.

Referring to FIG. 2, nose cone portion 12 defines an axially aligned recess 14 with an opening through its rear end which receives one end of rod portion 13. Rod 13 includes axially spaced openings 13c which serve as a well for adhesive for firmly mounting the nose cone. Thus, liquid adhesive 18 such as melted rubber (e.g., silicone rubber of the type produced by Dow Corning Corporation under the name Silastic rubber) is deposited in openings 13c and around the rod periphery to contact the inner surface of the nose cone and is solidified to form a solid adhesive bridge between the rod portion and the nose cone portion.

As set forth above, the present device is particularly useful in measuring the effective sphincter muscle of an animal so that an appropriately sized contraceptive device of the foregoing type may be used. Thus, to simulate this device and to minimize irritation during measurement, it is preferable to form nose cone portion 12 of a flexible material, such as natural or artificial rubber, e.g., Silastic rubber. In the device illustrated in the drawing, the rod portion 13 projects into the nose cone past ring 12b. The diameter of the inner surface of the ring is substantially larger than that of rod 13 so that the cross-sectional area simulates the corresponding cross-sectional area of the intra-vaginal device of our aforementioned co-pending application. Since the nose cone portion is formed of a flexible material, it is compressible at least in the area of the ring to minimize irritation during use.

The nose cone portion includes a front wall of enlarged thickness compared to the remainder of the wall to provide sufficient strength so that, upon meeting resistance, the front end 13b of elongate portion 13 does not pierce the nose cone.

The present measuring device is urged to the anterior of the vaginal sphincter muscle by grasping the same by rod portion 13. It includes sufficient rigidity to be shape-retaining against moderate resistance from the vaginal lining. For this purpose, the stiffness may be provided by forming hollow rod portion 13 of relatively stiff material such as nylon. This hollow configuration is illustrated in FIG. 4. In an alternate embodiment, elongate member 13 includes a relatively flexible exterior hollow rod with an internal solid stiffener 16.

Rod portion 13 also serves to measure the length of the animal's vagina. For this purpose, the device may be grasped by nose portion 12 while the free end of rod portion 13 is inserted into the animal's vagina. To avoid irritation during such measurement, a round soft plug 17 is seated at the free end of rod 13. It is suitably formed of the same type material as nose cone 12.

For measurement of the length of the animal's vagina, rod portion 13 is longer than the animal's vagina and includes externally visible spaced markings for measuring the length of the same. In the embodiment of FIGS. 3 and 4, such markings are placed directly on the external surface of rod 13. In the embodiment of FIGS. 1 and 2, such markings are made upon stiffener 16 and are externally visible through a translucent or transparent rod portion 13.

A device of the foregoing type is used in a trial and error method for measuring the effective diameter of the vaginal sphincter muscle. Thus, the free end of rod 13 is grasped as a handle and the nose portion is inserted through the animal's vulva into the animal's vagina until the intermediate ring 12b passes anterior to the sphincter muscle. It has been found that the effective sphincter muscle size for the contraceptive device is indicated when the measuring device causes a marked build-up of resistance against anterior movement transmitted to the grasped rod 13 upon contact of ring 12b with the sphincter muscle and a distinct release of the resistance after passage through the muscle. Thus, the method includes repeating of the insertion step with different measuring devices having intermediate rings of successively increased diameters until one is found which causes such marked build-up of resistance and subsequent release.

It is apparent that the dimensions of the measuring device is varied to a great extent depending upon the size of the animal to be measured. For example, for use in the dog, ring 12b may vary from 8 to 50–60 millimeters. It typically is in the range of 12 to 43 millimeters with an average size of 16 to 37 millimeters. The length of the device may vary from 25 millimeters to 200 millimeters. In general, the rod 13 is substantially longer than the length of the nose cone portion to permit the ring to pass anterior of the vaginal sphincter muscle. Thus, rod 13 is typically at least two to four times longer than the length of the nose cone portion.

The tapers of nose cone portion 12 may vary depending upon the animal to be measured. A typical range of tapers is from four to eight axial units for each radial unit of taper.

The diameter of the rod portion 13 may be varied. However, it has been found that if the outer diameter of the rod is greater than about 9 millimeters, a length measurement will cause irritation unless plug 17 includes a diameter larger than 9 millimeters.

Although the foregoing device has been illustrated with the handle in the form of a cylindrical rod, it is to be understood that other forms of the handle may be employed so long as the portion which is inserted into the vagina is of a shape which does not cause irritation. Also, the device may be formed with the nose cone portion and elongate portion in one piece so long as it is sufficiently rigid to permit insertion of the device. This embodiment is not preferable as the one in which the nose cone is formed of a relatively flexible material in comparison to that of rod 13. Also, if the shape of the portion of the device of our aforementioned application corresponding to the present nose cone portion is modified, as into an oval cross-section, the shape of the nose cone would be correspondingly modified.

We claim:

1. In a trial and error method for measuring the effective diameter of the vaginal sphincter muscle of an animal of the type having a vagina terminating at the posterior end in a normally closed vulva and at the anterior end in a normally closed cervix and having a vaginal sphincter muscle therebetween using a device with a nose cone portion having a rounded blunt free end mounted to an elongate handle, said nose cone portion including an intermediate ring of maximum diameter, the steps of a. grasping one of said measuring devices by the handle and inserting the nose cone portion through the animal's vulva into the animal's vagina until said intermediate ring passes anterior to said sphincter muscle, and b. repeating step (a) with different measuring devices having intermediate rings of successively increased diameters until a measuring device is tried which causes a marked build-up of resistance against anterior movement of the device upon contact of said intermediate ring with the sphincter muscle and a distinct release of the resistance after passage through the muscle.

* * * * *